United States Patent
Tojo et al.

(10) Patent No.: US 11,051,677 B2
(45) Date of Patent: Jul. 6, 2021

(54) INSERTION SYSTEM

(71) Applicant: OLYMPUS CORPORATION, Tokyo (JP)

(72) Inventors: Ryo Tojo, Hachioji (JP); Hiromasa Fujita, Hachioji (JP); Tetsuya Morishima, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 369 days.

(21) Appl. No.: 16/158,371

(22) Filed: Oct. 12, 2018

(65) Prior Publication Data
US 2019/0046010 A1   Feb. 14, 2019

Related U.S. Application Data

(63) Continuation of application No. PCT/JP2016/061820, filed on Apr. 12, 2016.

(51) Int. Cl.
*A61B 1/00* (2006.01)
*A61B 1/005* (2006.01)

(52) U.S. Cl.
CPC .......... *A61B 1/00078* (2013.01); *A61B 1/00* (2013.01); *A61B 1/00057* (2013.01); *A61B 1/0057* (2013.01)

(58) Field of Classification Search
None
See application file for complete search history.

(56) References Cited

U.S. PATENT DOCUMENTS

| 4,601,283 | A | * | 7/1986 | Chikama | A61B 1/31 219/201 |
| 5,357,979 | A | * | 10/1994 | Imran | A61M 25/0054 600/585 |
| 5,482,029 | A | | 1/1996 | Sekiguchi et al. | |

(Continued)

FOREIGN PATENT DOCUMENTS

| JP | H06-70879 A | 3/1994 |
| JP | H06-292652 A | 10/1994 |
| WO | WO 2015/198761 A1 | 12/2015 |

OTHER PUBLICATIONS

Chinese Office Action dated Apr. 23, 2020 in Chinese Patent Application No. 201680084562.6.
(Continued)

*Primary Examiner* — Timothy J Neal
(74) *Attorney, Agent, or Firm* — Scully, Scott, Murphy & Presser, P.C.

(57) ABSTRACT

An insertion system includes an insertion section and a rigidity variable portion provided in the insertion section. The rigidity variable portion includes a superelastic alloy member whose rigidity starts changing from a high-rigidity state to a low-rigidity state at a temperature, which varies with a degree of bending of the superelastic alloy member, and a heating member capable of switching between presence and absence of heating of the superelastic alloy member. The insertion system also includes a bending state detection sensor that detects a bending state of the rigidity variable portion, and a rigidity variable controller that controls switching between presence and absence of heating of the superelastic alloy member by the heating member to control the temperature of the superelastic alloy member.

8 Claims, 8 Drawing Sheets

(56) References Cited

U.S. PATENT DOCUMENTS

| | | | | |
|---|---|---|---|---|
| 2002/0013550 A1* | 1/2002 | Unsworth | ............ | A61B 1/0058 604/113 |
| 2006/0064055 A1* | 3/2006 | Pile-Spellman | ............................ | A61M 25/0105 604/95.05 |
| 2007/0149852 A1* | 6/2007 | Noguchi | .............. | A61B 1/0051 600/144 |
| 2010/0160724 A1* | 6/2010 | Prisco | .................... | A61B 34/35 600/101 |
| 2017/0079508 A1* | 3/2017 | Ikeda | .................. | A61B 1/0055 |

OTHER PUBLICATIONS

English translation of International Preliminary Report on Patentability dated Oct. 25, 2018 together with the Written Opinion received in related International Application No. PCT/JP2016/061820.

International Search Report dated Jul. 12, 2016 issued in PCT/JP2016/061820.

* cited by examiner

INSERTION SYSTEM

CROSS-REFERENCE TO RELATED APPLICATIONS

This application is a Continuation Application of PCT Application No. PCT/JP2016/061820, filed Apr. 12, 2016, the entire contents of which are incorporated herein by reference.

BACKGROUND OF THE INVENTION

1. Field of the Invention

The present invention relates to an insertion system.

2. Description of the Related Art

The endoscope system disclosed in, for example, Jpn. Pat. Appln. KOKAI Publication No. 6-70879 includes a variation portion (e.g. a shape-memory alloy) that varies, for each segment, the rigidity of a flexible tube placed in an insertion section of an endoscope and a database that stores flexibility control patterns corresponding to rigidity combinations for each segment. In the endoscope system, the rigidity of a segment is controlled in accordance with one flexibility control pattern selected by an operator from among the flexibility control patterns displayed on a display. The insertion section is thus improved in its insertability. Note that a superelastic alloy can be used as one example of the variation portion.

BRIEF SUMMARY OF THE INVENTION

An insertion system includes: an insertion section to be inserted into an insertion target; a rigidity variable portion provided in the insertion section and including a superelastic alloy member whose rigidity finishes changing from a low-rigidity state to a high-rigidity state with a change from a temperature that is lower than a first temperature to a temperature that is equal to or higher than the first temperature and starts changing from the high-rigidity state to the low-rigidity state with a change to a temperature that is equal to or lower than a second temperature that is lower than the first temperature, the second temperature varying with a degree of bending of the superelastic alloy member, and a heating member capable of switching between presence and absence of heating of the superelastic alloy member; a bending state detection sensor that detects a bending state including information of the degree of bending of the rigidity variable portion; and a rigidity variable controller that sets a target temperature to maintain the superelastic alloy member in the high-rigidity state at a temperature that is lower than the first temperature and equal to or higher than the second temperature, based upon the information of the degree of bending after the rigidity of the superelastic alloy member changes to the high-rigidity state, and controls switching between presence and absence of heating of the superelastic alloy member by the heating member to thereby control the superelastic alloy member to change to the target temperature.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will be described in detail below with reference to the drawings. In some of the drawings, some of the members are excluded therefrom for the sake of clarity of the drawings.

First Embodiment

A first embodiment will be described with reference to FIGS. 1-5.

Figure 1:
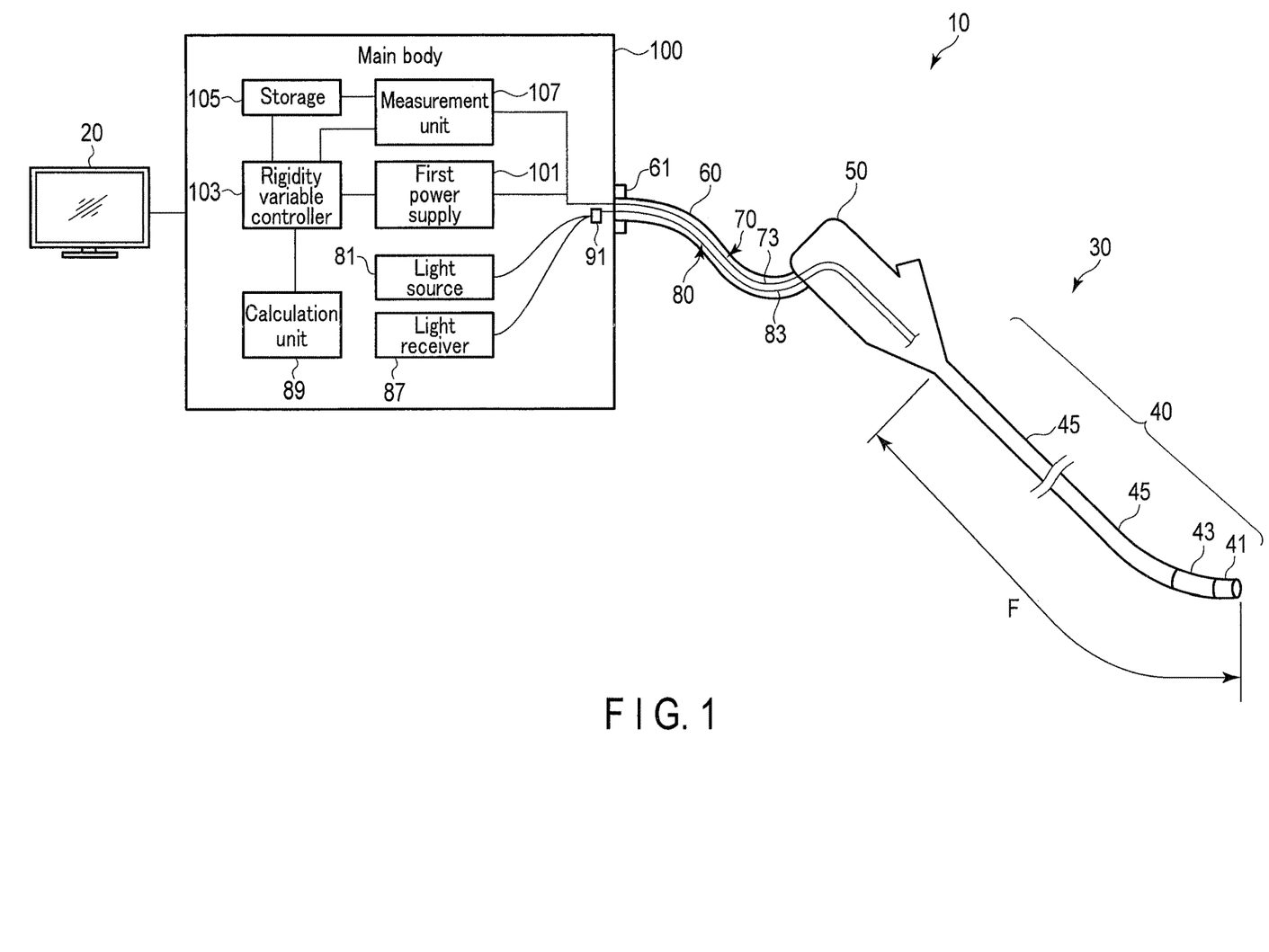
FIG. 1 is a schematic diagram of an insertion system according to a first embodiment of the present invention.

As shown in FIG. 1, an insertion system 10 includes a display 20, an insertion apparatus 30, a rigidity variable portion 70, a bending state detection sensor 80, and a main body 100.

The display 20 displays an image picked up by an imaging section (not shown) that is built in the distal end of an insertion section 40 placed in the insertion apparatus 30. The display 20 is a generally-used display device such as a liquid crystal display, a CRT display, and an organic EL display.

The insertion apparatus 30 according to the present embodiment will be described as a medical flexible endoscope, for example; however, it need not be limited thereto. The insertion apparatus 30 has only to include a flexible insertion section 40 to be inserted into an insertion target, such as a catheter and a treatment instrument. The insertion section 40 according to the present embodiment has only to be flexible and bendable. The insertion target is not limited to human beings but may be animals, structures, and the like.

The insertion apparatus 30 includes the insertion section 40 to be inserted into an insertion target, a control section 50 connected to the proximal end of the insertion section 40 to control the insertion apparatus 30, and a cord 60 connected to the control section 50. The cord 60 includes a connector 61 that is placed at the end of the cord 60 and detachable from the main body 100.

The insertion section 40 is, for example, hollow and elongated. The insertion section 40 includes, from its distal end toward its proximal end, a distal hard section 41 in which various internal members suitable for use in the insertion apparatus 30 are arranged, a bendable section 43 that can be bent by a desired amount in a desired direction, and a flexible tube section 45 that is flexible and bent by an external force. The internal members include, for example, the imaging section. The bendable section 43 is connected to a bend control section (not shown) placed in the control section 50 through a control wire (not shown) placed in the interior of the insertion section 40. The control wire is pulled by the control of the bend control section to allow the bendable section 43 to be bent by a desired amount in a desired direction.

An operator who operates the insertion system 10 grips the control section 50 with one hand. The operator inserts the insertion section 40 into an insertion target from an opening (e.g. a patient's mouth) of the insertion target. Then, the operator observes and treats the interior of the insertion target while visually checking an image picked up by the imaging section and displayed on the display 20.

Figure 2:
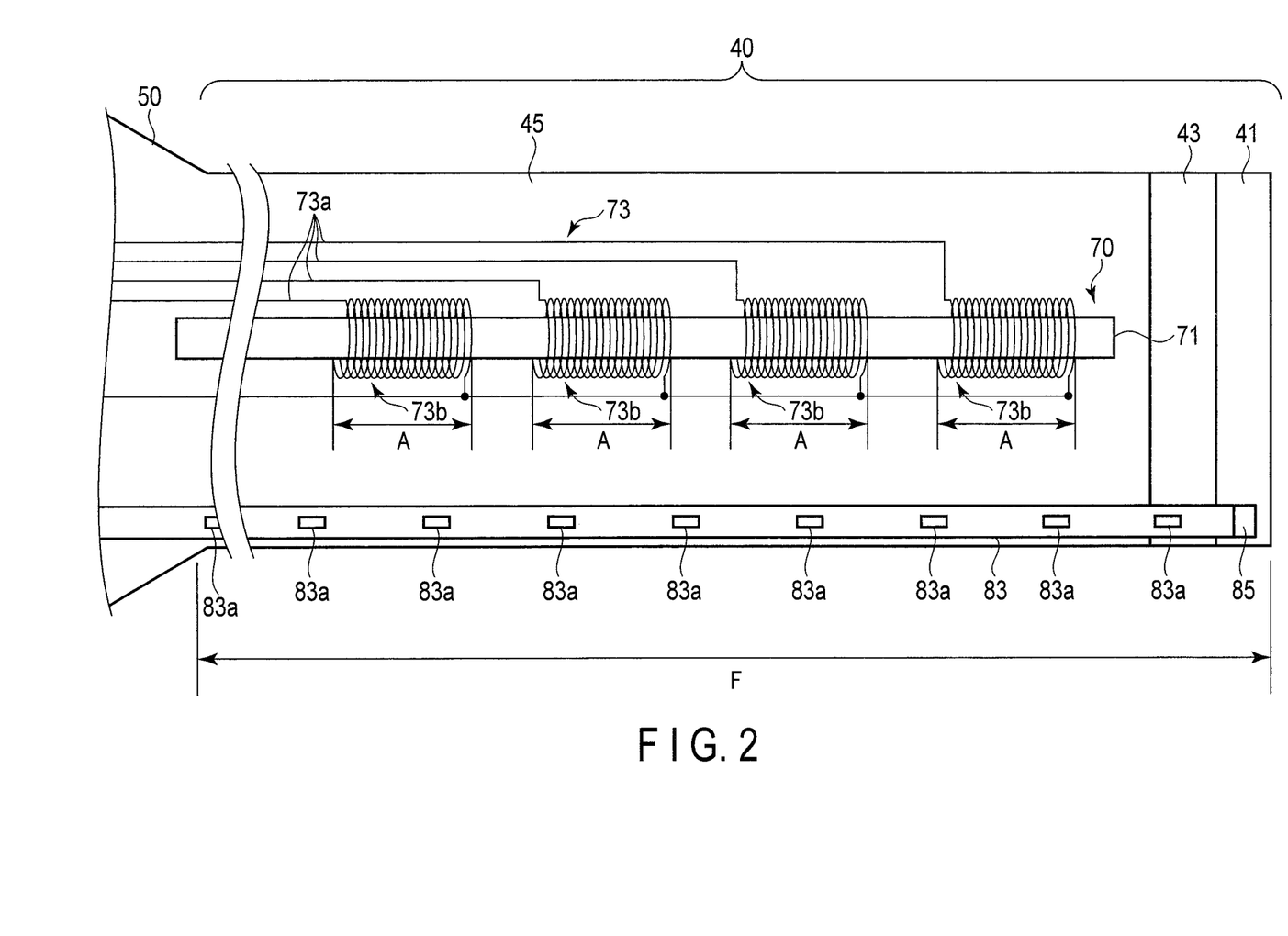
FIG. 2 is a diagram showing a configuration of each of a bending state detection sensor and a rigidity variable portion in an insertion section shown in FIG. 1.

As shown in FIGS. 1 and 2, the rigidity variable portion 70 is placed in a portion of the insertion section 40 whose rigidity can be varied by the rigidity variable portion 70, and thus the rigidity of the portion can be varied. The portion is, for example, the whole of the flexible tube section 45. The rigidity variable portion 70 includes, for example, a superelastic alloy 71 and a heater 73 capable of heating the superelastic alloy 71.

The superelastic alloy 71 is built in the flexible tube section 45 along the entire length of the flexible tube section 45, for example. Assume in the present embodiment that, for example, one superelastic alloy 71 is placed. The superelastic alloy 71 has the property of changing the rigidity from the low state to the high state by heating of the heater 73. Hereinafter, a state in which the rigidity of the rigidity variable portion 70 (e.g. the superelastic alloy 71) is low will be referred to as a low-rigidity state and a state in which the rigidity of the rigidity variable portion 70 (e.g. the superelastic alloy 71) is high will be referred to as a high-rigidity state. In the low-rigidity state, the superelastic alloy 71 is deformed into a soft state in which it is easily deformed by an external force, and has a low elastic coefficient, thus providing relatively low hardness for the flexible tube section 45 that is a portion in which the superelastic alloy 71 is placed. The soft state is, for example, a bendable state. In the high-rigidity state, the superelastic alloy 71 is deformed into a hard state with predetermined hardness against an external force, and has a high elastic coefficient, thus providing relatively high hardness for the flexible tube section 45 that is a portion in which the superelastic alloy 71 is placed. The hard state may be, for example, a linear state. The external force means force by which the superelastic alloy 71 is deformed, and gravity is considered to be part of the external force. The superelastic alloy 71 has the property of changing from the high-rigidity state to the low-rigidity state by cooling. The cooling in the present embodiment is natural cooling.

The heater 73 is built in the insertion apparatus 30 from the connector 61 to the flexible tube section 45. The heater 73 includes, for example, one or more heating wires 73*a* that extend from the connector 61 to a desired position in the flexible tube section 45 and turn back to the connector 61 from the desired position. In the present embodiment, it is assumed that the heater 73 includes four heating wires 73*a*. One end of each of the heating wires 73*a* and the other end thereof are electrically connected to a first power supply 101 built in the main body 100. The heating wires 73*a* are electrically insulated from one another. For the insulation, the heating wires 73*a* are covered with a first insulation film (not shown). The first insulation film prevents a short circuit from being caused between the heating wires 73*a*. The superelastic alloy 71 is covered with a second insulation film (not shown), excluding a portion to be heated that will be described later. The second insulation film prevents a short circuit from being caused between the heating wires 73*a* and the superelastic alloy 71. Note that the second insulation film can be omitted if the first insulation film has only to be placed. The placement of the first and second insulation films is not particularly restrictive if insulation is performed. The heating wires 73*a* generate heat by current flowing from the first power supply 101. Each of the heating wires 73*a* includes a wound portion 73*b* that winds the superelastic alloy 71 at a desired position. For example, the inner periphery of the wound portion 73*b* is brought into close contact with the outer surface of the superelastic alloy 71. The wound portions 73*b* are displaced apart from each other in the longitudinal direction of the insertion section 40. In other words, a space is formed between the wound portions 73*b*. The wound portions 73*b* are arranged within a range in which the rigidity of the superelastic alloy 71 is variable and, in other words, they are arranged within a range in which the rigidity of the flexible tube section 45 is variable in association with that of the superelastic alloy 71.

The range in which the rigidity of the flexible tube section 45 is variable, and the length of the superelastic alloy 71, the number of superelastic alloys 71, the position of the superelastic alloy 71, the number of heating wires 73*a*, the length of (the number of turns of) the wound portions 73*b*, the position of the wound portions 73*b*, and the number of wound portions 73*b*, which are involved with the range, are appropriately set to desired values in accordance with, for example, the insertion target, the procedures of the insertion apparatus 30, the use application of the insertion apparatus 30, or a portion (segment) capable of varying the rigidity of the insertion section 40. One heating wire 73 may include would portions 73*b*. The number of portions (segments) capable of varying the rigidity of the insertion section 40 may be one.

The wound portions 73*b* generate heat by current flowing from the first power supply 101. The heat is transmitted to the superelastic alloy 71 from the wound portions 73*b* to heat the superelastic alloy. Here, the portion to be heated in the superelastic alloy 71 is referred to as a heating target. The heating target is a portion that is covered chiefly with the wound portions 73*b*. The temperature of the heating target increases by heat, and accordingly the temperature of the superelastic alloy 71 partially increases. When the temperature of the superelastic alloy 71 increases by heat, the rigidity of the heating target increases, so that the rigidity of a portion of the flexible tube section 45 in which the heating target is placed increases. When the heating is stopped and the temperature of the heating target is decreased by natural cooling, the rigidity of the target portion decreases, so that the rigidity of the portion of the flexible tube section 45 in which the heating target is placed increases. Since the wound portions 73*b* are not in contact with one another, the rigidity of the insertion section 40 including the flexible tube section 45 can be varied partially and selectively. This rigidity variable portion 70 can vary the rigidity of at least part of the insertion section 40 by the rigidity of the superelastic alloy 71 that can be varied by temperature.

As shown in FIGS. 1 and 2, the bending state detection sensor 80 detects and computes a bending state of a desired shape detection range (referred to as range F hereinafter) set in the insertion apparatus 30. In the present embodiment, an example of the bending state will be described as a bending amount. The bending state may be a bending shape including a bending amount (the degree of bending) and a bending direction. In the present embodiment, the range F is defined as, for example, the whole of the insertion section 40. The range F may be part or the whole of the insertion apparatus 30, like the flexible tube section 45 in which the superelastic alloy 71 is placed. The bending state detection sensor 80 according to the present embodiment includes a fiber sensor, and is incorporated into the insertion section 40 and bent integrally with the insertion section 40 to detect the bending amount of the insertion section 40. Specifically, the bending state detection sensor 80 detects a variation of the bending amount of the insertion section 40 based upon a variation added to an optical fiber 83 in association with the variation of the bending amount of the insertion section 40.

The bending state detection sensor 80 includes a light source 81, the optical fiber 83 in which one or more detection targets 83*a* are arranged, a reflector 85 such as a mirror, a light receiver 87, a calculation unit 89, and a light branching unit 91. The bending state detection sensor 80 is a sensor that detects a relationship in characteristics between light input to the optical fiber 83 and light output therefrom to obtain the bending amount of the insertion section 40.

In the present embodiment, the detection targets 83*a* are arranged in the optical fiber 83. The detection targets 83*a* are arranged in different positions in the longitudinal direction of the optical fiber 83. In this case, the bending amount of the insertion section 40 can be detected. Note that one detection target 83*a* may be arranged in one optical fiber 83 and, in this case, two or more optical fibers 83 are placed. Assume that the detection targets 83*a* are arranged in the same position in the longitudinal direction of the optical fiber 83 or in positions close to one another and in different positions in the axial rotation direction in the longitudinal direction thereof. In this case, the degree and direction of bending can be detected by the combinations of detection results of the detection targets 83*a*.

The light source 81 is built in the main body 100 to radiate light toward the optical fiber 83. The light source 81, which differs from a light source for illumination, radiates light to detect a bending amount of the insertion section 40. The light source 81 includes, for example, at least one of a lamp such as a xenon lamp and a halogen lamp, and a semiconductor light source such as an LED and an LD. The optical fiber 83 is built in the insertion apparatus 30 to the distal end of the flexible tube section 45 through the connector. 61 to guide light. The optical fiber 83 is flexible. Since the bending state detection sensor 80 detects the bending amount of the insertion section 40, the detection targets 83*a* are disposed in the insertion section 40, for example. In other words, the bending state detection sensor 80 detects the shape of a portion in which the detection targets 83*a* are disposed.

The reflector 85 is placed at the distal end of the optical fiber 83. The reflector 85 reflects the light guided by the optical fiber 83 to return the light to the proximal end of the optical fiber 83.

The light receiver 87 and the calculation unit 89 are arranged in the main body 100. The light receiver 87 may include, for example, a spectroscopic element such as a spectroscope and a color filter, and a light-receiving element such as a photodiode. The calculation unit 89 is configured by a hardware circuit including an ASIC and the like. The calculation unit 89 can be configured by a processor. When the calculation unit 89 is configured by a processor, a program code for causing the processor to function as the calculation unit 89 is stored in an internal memory or an external memory (neither of which is shown) to which the processor can gain access.

The light source 81, the light receiver 87, and the proximal end of the optical fiber 83 are optically connected. The light branching unit 91 includes, for example, an optical coupler or a half mirror. The light branching unit 91 guides light radiated from the light source 81 to the optical fiber 83 and guides return light guided by the optical fiber 83 to the light receiver 87. The light branching unit 91 is placed in the main body 100.

As the insertion section 40 is bent, the optical fiber 83 is bent. Accordingly, part of the light transmitted through the optical fiber 83 is radiated (leaked) to the outside through the detection targets 83*a*. Specifically, the detection targets 83*a* are arranged on one side of the optical fiber 83 and causes part of the light transmitted to exit to the outside according to the bending of the optical fiber 83. In other words, the detection targets 83*a* vary the optical characteristics of the optical fiber 83, such as the light transmission amount thereof. An optical signal including information about variations in the light transmission amount is converted to an electrical signal by the light receiver 87 and the electrical signal is sent to the calculation unit 89. Based upon the electrical signal, the calculation unit 89 calculates a bending amount of the insertion section 40 in the actually bent portion. The calculation unit 89 inputs the calculated bending amount of the insertion section 40 to a rigidity variable controller 103 placed in the main body 100.

The light transmission amount has been given as an example of the varying optical characteristics. However, the varying optical characteristics are not limited to the light transmission amount, but an optical state such as spectrum and polarization waves may be given and, in this case, the bending state detection sensor 80 has only to detect an optical state such as spectrum and polarization waves. The detection targets 83*a* may be configured by, for example, a material that reduces the intensity (amount) of light guided through the optical fiber 83, such as a light absorber. The detection targets 83*a* may also be configured by, for example, a material that absorbs light guided through the optical fiber 83 and emits light whose wavelength range differs from the guided light, such as a fluorescent substance.

The range F will now be described. Assume here that the detection targets 83*a* each have a length of 5 mm, for example, in the longitudinal axis direction of the optical fiber 83. In each of the detection targets 83*a*, its own bending amount is detected. However, actually, only the detection target 83*a* having a length of 5 mm, for example, is not bent. A certain range (e.g. a length of 60 mm) in the longitudinal axis direction of the optical fiber 83 is also bent due to the structure, material, or the like of the optical fiber 83 itself or a member incorporating the optical fiber 83. It can thus be considered that the detection target 83*a* detects not only the bending amount of a position where the detection target 83*a* is present, but also the bending amount of a certain range corresponding to 30 mm of each of the front and rear portions of the detection target 83*a*, for example, in the longitudinal axis direction of the optical fiber 83, i.e. a range of 60 mm. Thus, the range including a range that is substantially equal to the bending amount detected by the detection target 83*a* is defined as range F.

As shown in FIG. 2, the range F overlaps ranges A in which the rigidity variable portion 70 varies the rigidity of the flexible tube section 45. The ranges A represent, for example, portions to be heated that are wound by the wound portion 73b. Therefore, the bending state detection sensor 80 can detect a bending amount of the insertion section 40, and detect and calculate a bending state of the rigidity variable portion 70, or specifically a bending amount of each of the portions to be heated of the superelastic alloy 71. For example, the bending state detection sensor 80 performs in real time the detection and calculation and the input of the bending amount to the rigidity variable controller 103. In FIG. 2, the ranges A each represent the same range of the corresponding wound portion 73b, but a range that is wider than the wound portion 73b can be heated by heat conduction. In this case, the range in which the superelastic alloy 71 is changed into a high-rigidity state by heating of the wound portion 73b is defined as range A. Upon receiving an operation start instruction from an instruction unit (not shown) such as a switch, the bending state detection sensor 80 continues performing the detection, calculation, and input. The bending state detection sensor 80 may detect and calculate at least one of the bending state (e.g. the bending amount) of the insertion section 40 and that of the rigidity variable portion 70. The detection and calculation of the bending amount of the rigidity variable portion 70 is substantially the same as that of the bending amount of the insertion section 40. Thus, based on an electrical signal, the calculation unit 89 calculates a bending amount of the rigidity variable portion 70 in the actually bent portion. The calculation unit 89 inputs the calculated bending amount of the rigidity variable portion 70 to the rigidity variable controller 103. The range F is set to overlap the ranges A in which temperature is controlled in accordance with the bending state. If a bending amount of part of the range A is detected and can be considered to be equal to the bending amount of a range in which no bending amount is detected, the range F need not overlap all of the ranges A but can be set to overlap some of the ranges A. The main body 100 includes the first power supply 101, the rigidity variable controller 103, a storage 105, and a measurement unit 107.

The first power supply 101 applies a voltage to the heating wires 73a and causes current to flow through the heating wires 73a in order to heat the superelastic alloy 71 through the heating wires 73a.

The rigidity variable controller 103 is configured by, for example, a hardware circuit including an ASIC and the like. The rigidity variable controller 103 may be configured by a processor. When the rigidity variable controller 103 is configured by a processor, a program code for causing the processor to function as the rigidity variable controller 103 is stored in an internal memory or an external memory (neither of which is shown) to which the processor can gain access.

The rigidity variable controller 103 controls the current flowing from the first power supply 101 to the heating wires 73a based upon the bending amount of the rigidity variable portion 70 calculated by the calculation unit 89 and the temperature of the rigidity variable portion 70 measured by the measurement unit 107. The rigidity variable controller 103 controls the first power supply 101 to start supplying current to heat the superelastic alloy 71 and to adjust the amount of current.

Assume that the insertion section 40 is inserted into a lumen of an insertion target and bent along the shape of the lumen. The bending amount of the insertion section 40 is detected by the bending state detection sensor 80. Assume that there is a desired range in which the bending amount of the insertion section 40 becomes equal to or higher than a threshold value. The threshold value is stored in, for example, the storage 105 in advance. When the rigidity variable controller 103 controls the first power supply 101, current flows through the heater 73 within the distal end range of which the wound portions 73b are arranged in the desired range. The distal end range in the desired range indicates, for example, the front range of the front and rear two ranges in the longitudinal axis direction of the insertion section 40. Thus, the rigidity of the rigidity variable portion 70 in the distal end range in the desired range increases. Accordingly, when the insertion section 40 moves to a deep portion of the lumen of the insertion target, the insertion force into the insertion section 40 from the operator in the moving direction of the insertion section 40 becomes easy to transmit to the distal end of the insertion section 40. Then, the insertion section 40 is improved in its insertability.

Figure 3:
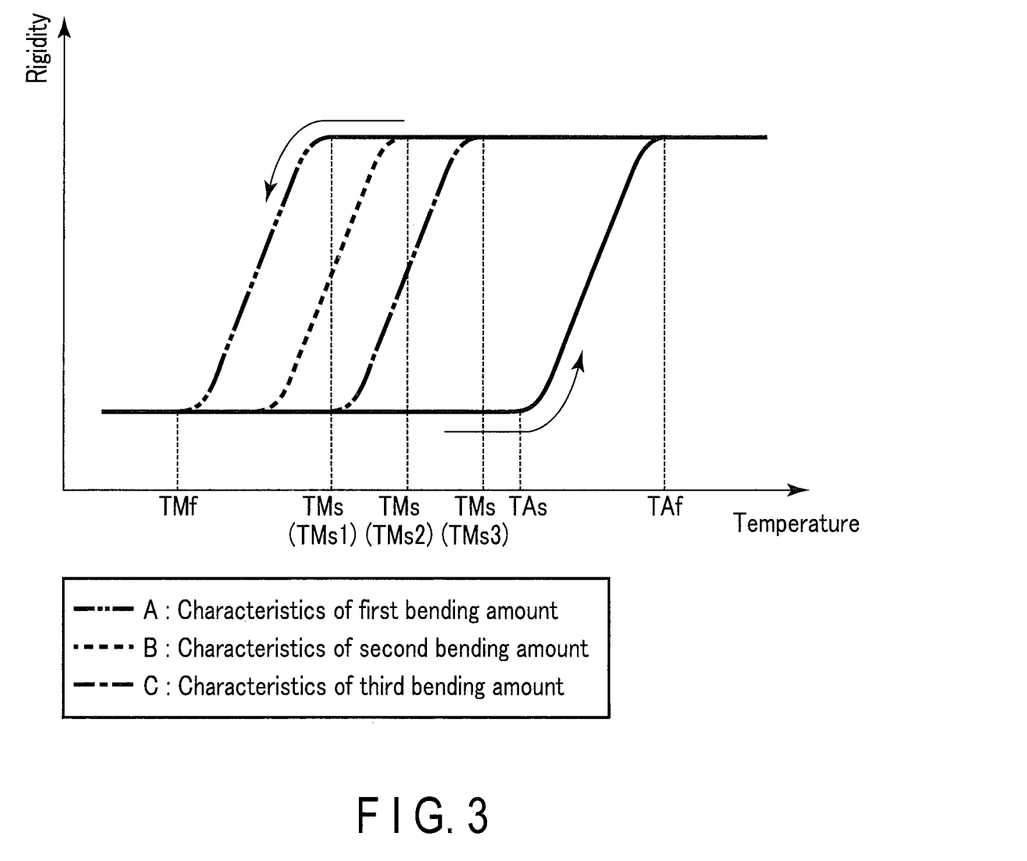
FIG. 3 is a graph showing the relationship between the temperature of a superelastic alloy and the rigidity thereof.

The rigidity variable controller 103 controls the rigidity (degree of flexibility) of the flexible tube section 45 based on the rigidity of the superelastic alloy 71. The rigidity of the superelastic alloy 71 is controlled by the temperature of the superelastic alloy 71. FIG. 3 shows the relationship between the temperature of the superelastic alloy 71 and the rigidity thereof. Since the superelastic alloy 71 is heated by the heating wires 73a, the responsiveness of a rigidity change in the superelastic alloy 71 to the heating is satisfactory. On the other hand, cooling time is longer than heating time, in the present embodiment, in particular, the cooling is natural cooling, and thus the responsiveness is bad. Furthermore, as shown in FIG. 3, the relationship between the temperature of the rigidity variable portion 70 (e.g. the superelastic alloy 71) and the rigidity thereof (e.g. the superelastic alloy 71) has a hysteresis. The hysteresis here means, for example, that the temperature to decrease the rigidity is lower than the temperature to increase the rigidity. Due to the responsiveness and hysteresis, it takes time to cool the superelastic alloy 71. If it takes time to cool the superelastic alloy 71, it takes time to change the superelastic alloy 71 from the high-rigidity state to the low-rigidity state. Accordingly, it also takes time to change the flexible tube section 45 from the high-rigidity state to the low-rigidity state.

Here, the temperature at which the rigidity variable portion 70 (e.g. the superelastic alloy 71) starts changing from the low-rigidity state to the high-rigidity state as shown in FIG. 3 is referred to as Temperature Austenite Start (hereinafter referred to as TAs). The temperature at which the rigidity variable portion 70 (e.g. the superelastic alloy 71) has finished changing from the low-rigidity state to the high-rigidity state is referred to as Temperature Austenite Finish (hereinafter referred to as TAf). The temperature at which the rigidity variable portion 70 (e.g. the superelastic alloy 71) starts changing from the high-rigidity state to the low-rigidity state is referred to as Temperature Martensite Start (hereinafter referred to as TMs). The temperature at which the rigidity variable portion 70 (e.g. the superelastic alloy 71) has finished changing to the low-rigidity state is referred to as Temperature Martensite Finish (hereinafter referred to as TMf). Note that the low-rigidity state may be a state in which the rigidity is the lowest and the high-rigidity state may be a state in which the rigidity is the highest.

The superelastic alloy 71 is in the low-rigidity state in the temperature range of equal to or lower than TMf.

TAs is equal to or higher than TMf and lower than TAf. In the temperature range of equal to or higher than TMf and lower than TAs, even though the temperature increases, the superelastic alloy 71 remains in the low-rigidity state without being influenced by the bending amount.

TAs is lower than TAf. In the temperature range of equal to or higher than TAs and lower than TAf, as the temperature increases from TAs to TAf, the superelastic alloy 71 increases in rigidity and changes from the low-rigidity state to the high-rigidity state.

The superelastic alloy 71 is in the high-rigidity state in the temperature range of equal to or higher than TAf.

TMs is lower than TAf and TAs. In the temperature range of equal to or higher than TMs and lower than TAf, even though the temperature decreases, the superelastic alloy 71 remains in the high-rigidity state without being influenced by the bending amount.

TMf is lower than TMs. In the temperature range of equal to or higher than TMf and lower than TMs, as the temperature decreases from TMs to TAf, the superelastic alloy 71 decreases in rigidity and changes from the high-rigidity state to the low-rigidity state.

The above-described cooling time means time required to decrease the temperature of the rigidity variable portion 70 (e.g. the superelastic alloy 71) from TAf to TMf through TMs. The rigidity of the superelastic alloy 71 in the high-rigidity state remains substantially unchanged whether the temperature of the superelastic alloy 71 is at TAf or TMs. In the present embodiment, therefore, in order to shorten the cooling time in consideration of the bad responsiveness and the hysteresis, the rigidity variable controller 103 performs control to decrease the temperature of the superelastic alloy 71 in advance to a target temperature (e.g. TMs) immediately without waiting after the temperature of the superelastic alloy 71 has reached TAf.

For descriptions, assume here that there are three bending amounts of the superelastic alloy 71 as shown in FIG. 3. These three bending amounts will be referred to as first to third bending amounts hereinafter. Assume that the first bending amount is smaller than the second bending amount and the second bending amount is smaller than the third bending amount.

As described above, in order to shorten the cooling time in consideration of the bad responsiveness and the hysteresis, the rigidity variable controller 103 needs to perform control to decrease the temperature of the superelastic alloy 71 to a target temperature (e.g. TMs), which is set to shorten the cooling time, after the temperature of the superelastic alloy 71 has reached TAf. However, the relationship between the temperature of the rigidity variable portion 70 (e.g. the superelastic alloy 71) and the rigidity of the rigidity variable portion 70 (e.g. the superelastic alloy 71) varies based on the bending state. For example, as shown in FIG. 3, the target temperature TMs varies with the first to third bending amounts. Here, TMs corresponding to the first to third bending amounts is referred to as TMs1, TMs2, and TMs3. TMs1 is lower than TMs2 and TMs2 is lower than TMs3. The rigidity variable controller 103 determines a target temperature based on the bending state of the rigidity variable portion 70 detected by the bending state detection sensor 80 and controls the temperature of the rigidity variable portion 70 at the target temperature TMs that varies with the bending state. Specifically, the rigidity variable controller 103 calculates the target temperature TMs (TMs1, TMs2, or TMs3) corresponding to the first to third bending amounts based upon the first to third bending amounts of the superelastic alloy 71 detected by the bending state detection sensor 80. After the temperature of the superelastic alloy 71 has reached TAf, the rigidity variable controller 103 controls the temperature of the superelastic alloy 71 to change to the calculated target temperature TMs (TMs1, TMs2, or TMs3). For the control, the rigidity variable controller 103 turns off the first power supply 101 to stop supplying current to the heating wires 73a. Thus, the heating is stopped, the natural cooling is executed, and the temperature of the superelastic alloy 71 decreases from TAf to the target temperature TMs (TMs1, TMs2, or TMs3).

If the bending amount of the rigidity variable portion 70 (e.g. the superelastic alloy 71) detected by the bending state detection sensor 80 is referred to as κ, the rigidity variable controller 103 calculates the target temperature TMs using a following equation (1).

$$TMs = f(\kappa) \tag{1}$$

Figure 4:
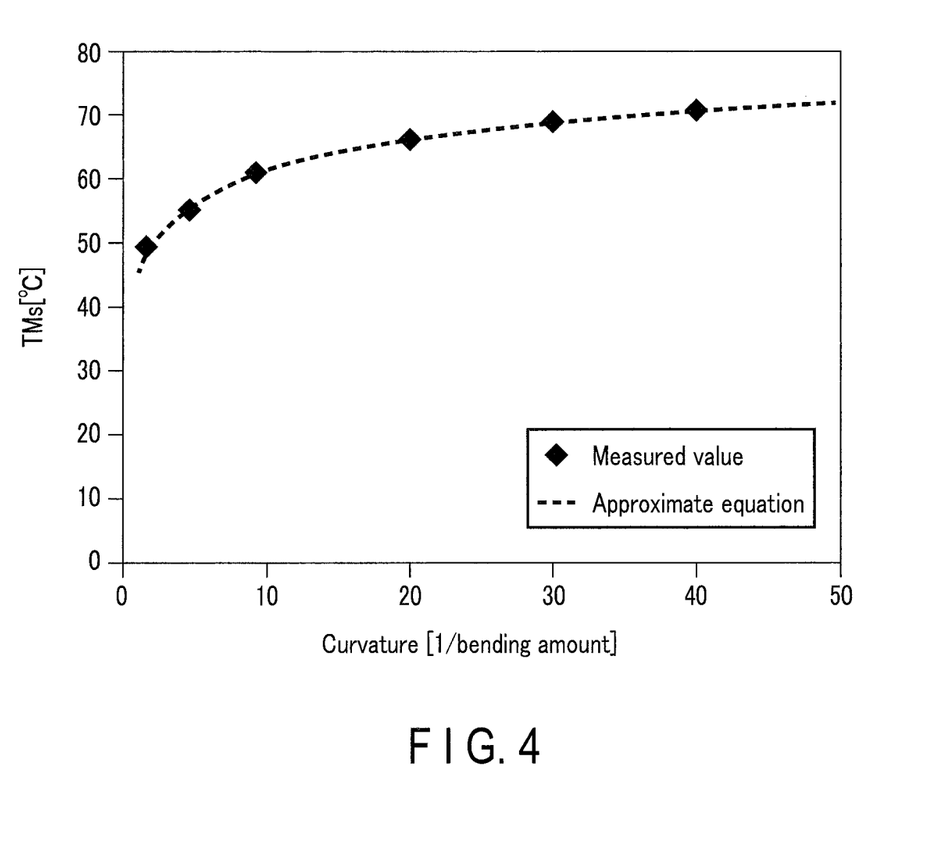
FIG. 4 is a graph showing the relationship between premeasured curvature (bending amount) and TMs corresponding to the bending amount.

The equation (1) may correspond to a following equation (2) based upon the relationship between the premeasured curvature (bending amount) of the rigidity variable portion 70 (e.g. the superelastic alloy 71) and TMs corresponding to the bending amount, as shown in FIG. 4, for example.

$$TMs = A \times \log_B \kappa + C \tag{2}$$

In the equation (2), A, B, and C are constants that depend upon the premeasured bending amount and TMs. The rigidity variable controller 103 thus calculates the target temperature TMs (TMs1, TMs2, or TMs3) using the equation (1) or (2). The dots shown in FIG. 4 indicate measured values, and the broken line is an approximate curve given by the equation (2).

The storage 105 stores the equation (1) or (2) in advance. Upon receiving the bending amount κ of the superelastic alloy 71 from the bending state detection sensor 80, the rigidity variable controller 103 gains access to the storage 105 and calculates the target temperature TMs based upon the bending amount κ of the superelastic alloy 71 and the equation (1) or (2). Then, based upon TMs, the rigidity variable controller 103 controls the first power supply 101, or specifically the current flowing through the heating wires 73a.

Note that the calculation of TMs is not limited to the above. The storage 105 may store, for example, a data table showing the relationship between x and its corresponding target temperature TMs. When the rigidity variable controller 103 receives the bending amount x of the superelastic alloy 71 from the bending state detection sensor 80, it may gain access to the storage 105 to calculate TMs corresponding to the bending amount κ from the data table.

The target temperature need not be limited to TMs. The target temperature may be increased and decreased with reference to TMs with the aim of controlling the rigidity of the insertion section 40. Assume that the target temperature is higher than TMs, for example. In this case, even though TMs varies with a sudden change in the bending amount of the insertion section 40 or variation occurs in the heating temperature of the superelastic alloy 71, the rigidity of the insertion section 40 is maintained in a stable state. When the target temperature is lower than TMs, the cooling time is shortened.

The storage 105 stores TAs, TAf, TMs (TMs1, TMs2, or TMs3) corresponding to the bending amount of the superelastic alloy 71, and TMf. The storage 105 stores threshold values that are criterion values for the bending amount of the flexible tube section 45 and the bending amount of the superelastic alloy 71 when the superelastic alloy 71, namely, the flexible tube section 45, changes from the low-rigidity state to the high-rigidity state, and threshold values that are criterion values for the bending amount of the flexible tube section 45 and the bending amount of the superelastic alloy 71 when the superelastic alloy 71, namely, the flexible tube section 45, changes from the high-rigidity state to the low-rigidity state.

The storage 105 stores the relationship between the previously-obtained resistance value of the heating wires 73a and the temperature of the heating wires 73a. The measurement unit 107 includes a current detector (not shown) that detects current flowing through the heating wires 73a and a voltage detector (not shown) that detects a value of voltage applied to the heating wires 73a. The rigidity variable controller 103 calculates a resistance value of the heating wires 73a based upon the current value detected by the current detector of the measurement unit 107 and the voltage value detected by the voltage detector of the measurement unit 107. The measurement unit 107 gains access to the storage 105 to calculate the temperature of the heating wires 73a that corresponds to the calculated resistance value. After that, the measurement unit 107 outputs the calculated temperature to the rigidity variable controller 103. Since the heating wires 73a are in intimate contact with the superelastic alloy 71, the temperature of the heating wires 73a is considered to be the same as or approximate to that of the superelastic alloy 71. The temperature of the superelastic alloy 71 is thus measured individually through the temperature of the heating wires 73a. The measurement unit 107 and the rigidity variable controller 103 always perform an operation about the measurement.

Note that the measurement unit 107 may include a temperature sensor such as a thermocouple and a thermistor that is placed directly in the superelastic alloy 71 to measure the temperature of the superelastic alloy 71 directly. Thus, the measurement unit 107 can measure the temperature of the superelastic alloy 71 with precision. The measurement unit 107 may measure the heating time or the cooling time of the superelastic alloy 71. The rigidity variable controller 103 may estimate and control the temperature of the superelastic alloy 71 based upon the measurement time of the measurement unit 107. For example, the rigidity variable controller 103 maintains the temperature of the superelastic alloy 71 at TMs or its neighborhood to maintain the high-rigidity state until the superelastic alloy 71 needs to change from the high-rigidity state to the low-rigidity state.

An operation of the insertion system 10 will be described below using a flowchart shown in FIG. 5. The flowchart is directed to a process for one segment (e.g. one portion to be heated) of the flexible tube section 45, and the same process is performed for the respective segments of the flexible tube section 45.

Assume that, in the initial state, the superelastic alloy 71 and the flexible tube section 45 are in the low-rigidity state, for example. In this state, the insertion section 40 is inserted into a lumen of an insertion target and bent along the shape of the lumen. When the insertion section 40 is inserted into the insertion target, the bending amount of the insertion section 40 is detected by the bending state detection sensor 80. The range F of the bending state detection sensor 80 overlaps the range A of the superelastic alloy 71. Therefore, the bending amount of the superelastic alloy 71 is also detected by the bending state detection sensor 80 at the same time when the bending amount of the insertion section 40 is detected (Step 1).

The rigidity variable controller 103 determines whether to increase the rigidity of the superelastic alloy 71 based upon the threshold value stored in the storage 105 and the bending amount of the insertion section 40 detected by the bending state detection sensor 80 (Step 2). In this determination, a position in which the rigidity is increased, a threshold value of the bending amount, or the like is predetermined based upon the insertability of the insertion section 40 that moves toward a deep portion of a lumen, for example. When the rigidity variable controller 103 has determined that the rigidity of the superelastic alloy 71 need not be increased (No in Step 2), the operation of the insertion system 10 returns to Step 1.

When the rigidity variable controller 103 has determined that there is a portion in which the rigidity of the superelastic alloy 71 needs to be increased (Yes in Step 2), the rigidity variable controller 103 turns on the first power supply 101 to heat the superelastic alloy 71 by the heating wire 73a corresponding to the portion. Accordingly, the temperature of the superelastic alloy 71 increases toward TAf (Step 3).

The temperature of the superelastic alloy 71 is measured by the measurement unit 107 and the rigidity variable portion 70 based upon the temperature of the heating wire 73a. The rigidity variable controller 103 determines whether the temperature of the superelastic alloy 71 has reached TAf (Step 5). When the temperature of the superelastic alloy 71 does not reach TAf (No in Step 5), the operation of the insertion system 10 returns to Step 3.

When the temperature of the superelastic alloy 71 has reached TAf (Yes in Step 5), the superelastic alloy 71 finishes changing from the low-rigidity state to the high-rigidity state. In accordance with the change in the rigidity state of the superelastic alloy 71, the flexible tube section 45 also finishes changing from the low-rigidity state to the high-rigidity state.

In Steps 3 to 5, the superelastic alloy 71 is heated to change from the low-rigidity state to the high-rigidity state, and the flexible tube section 45 is changed from the low-rigidity state to the high-rigidity state by the superelastic alloy 71. Since the responsiveness of the superelastic alloy 71 to the heating is satisfied by the heating wires 73a, the superelastic alloy 71 and the flexible tube section 45 changes from the low-rigidity state to the high-rigidity state in a short time. Thus, for example, a desired portion of the insertion section 40 is hardened in a short time. Then, the insertion section 40 is improved in its insertability when the insertion section 40 moves toward, for example, a deep portion of a lumen of an insertion target. In Steps 3 to 5, therefore, the superelastic alloy 71 and the flexible tube section 45 is increased in their rigidity and the insertion section 40 is improved in its insertability.

Then, like in Step 1, the bending amount of the insertion section 40 and the bending amount of the superelastic alloy 71 are detected again by the bending state detection sensor 80 (Step 6). In Step 6, the bending amount of the superelastic alloy 71 is detected again because the bending amount of the superelastic alloy 71 may change through the process of Steps 3 to 6.

Due to the responsiveness of rigidity of the superelastic alloy 71 to cooling and the hysteresis, it takes time to cool the superelastic alloy 71. The cooling time means time required to decrease the temperature of the rigidity variable portion 70 (e.g. the superelastic alloy 71) from TAf to TMf through TMs. If it takes time to cool the superelastic alloy 71, it takes time to change the superelastic alloy 71 from the high-rigidity state to the low-rigidity state. Accordingly, it also takes time to change the flexible tube section 45 from the high-rigidity state to the low-rigidity state.

To shorten the cooling time, the rigidity variable controller 103 performs control to decrease the temperature of the superelastic alloy 71 to a target temperature (e.g. TMs) after the temperature of the superelastic alloy 71 has reached TAf in Step 5. The target temperature TMs varies with the bending amount of the superelastic alloy 71. Thus, the rigidity variable controller 103 calculates the target temperature TMs based upon the bending amount of the superelastic alloy 71 detected by the bending state detection sensor 80 and the equation (1) or (2) (Step 7).

In Step 6 precedent to Step 7, the bending amount of the superelastic alloy 71 has been detected again by the bending state detection sensor 80. Therefore, the rigidity variable controller 103 calculates TMs corresponding to the current bending amount of the superelastic alloy 71.

Then, the rigidity variable controller 103 turns off the first power supply 101. Accordingly, the temperature of the superelastic alloy 71 is controlled at the target temperature TMs. Here, the heating is stopped, the natural cooling is executed, and the temperature of the superelastic alloy 71 decreases toward the target temperature TMs (Step 8). The temperature of the superelastic alloy 71 is measured by the measurement unit 107 and the rigidity variable portion 70 based upon the temperature of the heating wires 73a (Step 9).

The rigidity variable controller 103 determines whether the temperature of the superelastic alloy 71 has reached the target temperature TMs (Step 10). When the temperature of the superelastic alloy 71 does not reach the target temperature TMs (No in Step 10), the operation of the insertion system 10 returns to Step 6.

When the temperature of the superelastic alloy 71 has reached the target temperature TMs (Yes in Step 10), preparations to cool the superelastic alloy 71 are made, or preparations to change the superelastic alloy 71 from the high-rigidity state to the low-rigidity state are made. Steps 6 to 10 are preparation periods to decrease the temperature of the superelastic alloy 71 from TAf to TMs and change the superelastic alloy 71 from the high-rigidity state to the low-rigidity state in a short time in order to shorten the cooling time. Steps 6 to 10 are also waiting periods to cause the superelastic alloy 71 to wait for changing to the low-rigidity state. The rigidity of the superelastic alloy 71 in the high-rigidity state remains unchanged whether the temperature of the superelastic alloy 71 is at TAf or TMs. Therefore, the flexible tube section 45 remains in the high-rigidity state, and the insertability is kept.

When the temperature of the superelastic alloy 71 has reached the target temperature TMs (Yes in Step 10), like in Step 1, the bending amount of the insertion section 40 and the bending amount of the superelastic alloy 71 are detected again by the bending state detection sensor 80 (Step 11). Step 11 is executed to determine whether the bending amount of the superelastic alloy 71 has varied, that is, whether to change TMs and also determine whether to change the superelastic alloy 71 from the high-rigidity state to the low-rigidity state.

The rigidity variable controller 103 determines whether to decrease the rigidity of the superelastic alloy 71 based upon the threshold value stored in the storage 105 and the bending amount of the insertion section 40 detected by the bending state detection sensor 80 (Step 12). In this determination, a position in which the rigidity is decreased, a threshold value of the bending amount, or the like is predetermined based upon a change in a portion (segment) whose rigidity should be increased as the insertion section 40 is inserted into a deep portion, removability of the insertion section 40 that retreats from the deep portion through the lumen, and the like. When the rigidity variable controller 103 determines that the rigidity of the superelastic alloy 71 need not be decreased (No in Step 12), the operation of the insertion system 10 returns to Step 6 and, in Step 8, the temperature of the superelastic alloy 71 is controlled to change to TMs. Then, the superelastic alloy 71 remains in the high-rigidity state.

When the rigidity variable controller 103 determines that the rigidity of the superelastic alloy 71 needs to be decreased (Yes in Step 12), the rigidity variable controller 103 turns off the first power supply 101 to finish keeping TMs. Therefore, the heating for keeping TMs is stopped, the natural cooling is executed, and the temperature of the superelastic alloy 71 decreases toward the target temperature TMf (Step 13). Thus, the superelastic alloy 71 starts changing from the high-rigidity state to the low-rigidity state and changes from the high-rigidity state to the low-rigidity state. The temperature of the superelastic alloy 71 is measured by the measurement unit 107 and the rigidity variable portion 70 based upon the temperature of the heating wires 73a (Step 14).

The rigidity variable controller 103 determines whether the temperature of the superelastic alloy 71 has reached TMf based upon a measurement result of the measurement unit 107 (Step 15). When the temperature of the superelastic alloy 71 does not reach TMf (No in Step 15), the operation of the insertion system 10 returns to Step 13.

When the temperature of the superelastic alloy 71 has reached TMf (Yes in Step 15), the superelastic alloy 71 is cooled, so that the superelastic alloy 71 finishes changing from the high-rigidity state to the low-rigidity state. In accordance with the change in the rigidity state of the superelastic alloy 71, the flexible tube section 45 also finishes changing from the high-rigidity state to the low-rigidity state.

In Steps 13 to 15, the superelastic alloy 71 is cooled, the cooling changes the superelastic alloy 71 from the high-rigidity state to the low-rigidity state, and the superelastic alloy 71 changes the flexible tube section 45 from the high-rigidity state to the low-rigidity state. In the present embodiment, when the superelastic alloy 71 and the flexible tube section 45 change from the high-rigidity state to the low-rigidity state, the temperature of the superelastic alloy 71 does not decrease continuously from TAf to TMf through TMs. The temperature of the superelastic alloy 71 decreases in advance to TMs calculated according to the bending amount of the superelastic alloy 71 from TAf, waits at TMs, and then decreases to TMf from TMs. Thus, the responsiveness of the superelastic alloy 71 to the cooling when the temperature of the superelastic alloy 71 decreases from TMs to TMf is more satisfactory than the responsiveness of the superelastic alloy 71 to the cooling when the temperature of the superelastic alloy 71 decreases continuously from TAf to TMf through TMs. Therefore, the superelastic alloy 71 and the flexible tube section 45 change from the high-rigidity state to the low-rigidity state in a short time. Then, a desired portion (segment) of the insertion section 40 is softened in a short time. Assume that the insertion section 40 has moved toward, for example, a deep portion in a lumen of an insertion target, so that the shape of the insertion section 40 has been changed. To improve the insertability of the insertion section 40, a range of a portion in the high-rigidity state and a range of a portion in the low-rigidity state need to vary with the shape of the lumen (the shape of the insertion section 40). In this case, too, a predetermined portion of the insertion section 40 can be changed into a low-rigidity state in a short time and the insertability of the insertion section 40 can be improved. In Steps 13 to 15, therefore, superelastic alloy 71 and flexible tube section 45 are decreased in their rigidity and the insertion section 40 is improved in its insertability.

The operation of the insertion system 10 may be returned to Step 1 or finished.

For example, in Steps 10 and 11, it is considered that when the superelastic alloy 71 waits at TMs1, the bending amount of the insertion section 40 varies and the bending amount of the superelastic alloy 71 varies. Assume that when the temperature of the superelastic alloy 71 is TMs1, the bending amount of the superelastic alloy 71 changes from the first bending amount to the second bending amount. In this case, like in Step 6, the bending amount of the superelastic alloy 71 is detected again by the bending state detection sensor 80, and like in Step 7, the rigidity variable controller 103 calculates TMs2 based upon the detected second bending amount of the superelastic alloy 71 and the equation (1) or (2). Then, in Step 8, the temperature of the superelastic alloy 71 increases toward the target temperature TMs2. Then, the operations after Step 9 are performed.

If the target temperature TMs1 remains unchanged when the bending amount of the superelastic alloy 71 changes from the first bending amount to the second bending amount, the rigidity of the superelastic alloy 71 decreases accidentally. Thus, the bending state detection sensor 80 detects the bending amount of the superelastic alloy 71 in real time and the rigidity variable controller 103 calculates TMs2 in real time based upon the detected bending amount of the superelastic alloy 71.

As described above, in the present embodiment, the temperature of the rigidity variable portion 70 is controlled to change to TMs based upon the bending state of the rigidity variable portion 70 detected in real time by the bending state detection sensor 80. In the present embodiment, therefore, the temperature can appropriately be controlled to change to TMs even though TMs varies with the bending state of the superelastic alloy 71. In the present embodiment, when the superelastic alloy 71 and the insertion section 40 changes from the high-rigidity state to the low-rigidity state, the temperature of the superelastic alloy 71 does not decrease continuously from TAf to TMf through TMs. The temperature of the superelastic alloy 71 decreases in advance to the preset TMs from TAf, waits at TMs, and then decreases to TMf from TMs. Thus, the responsiveness of the superelastic alloy 71 to the cooling when the temperature of the superelastic alloy 71 decreases from TMs to TMf can be made more satisfactory than the responsiveness of the superelastic alloy 71 to the cooling when the temperature of the superelastic alloy 71 decreases continuously from TAf to TMf through TMs. The superelastic alloy 71 and the flexible tube section 45 can thus change from the high-rigidity state to the low-rigidity state in a short time. Then, for example, a desired portion of the insertion section 40 can be softened in a short time. Assume that the insertion section 40 has moved toward, for example, a deep portion in a lumen of an insertion target, so that the shape of the insertion section 40 has been changed. To improve the insertability of the insertion section 40, a range of a portion in the high-rigidity state and a range of a portion in the low-rigidity state need to vary with the shape of the lumen (the shape of the insertion section 40). In this case, too, a predetermined portion of the insertion section 40 can be changed into a low-rigidity state in a short time and the insertability of the insertion section 40 can be improved. In other words, an appropriate range of the insertion section 40 can be changed into a low-rigidity state and a high-rigidity state in a short time and the insertion section 40 can be improved in its insertability.

In the present embodiment, the natural cooling is executed without using a cooling mechanism. When the natural cooling is executed, the temperature of the superelastic alloy 71 is decreased from TAf to TMs, the cooling time can be shortened. An increase in costs of the insertion system 10 and an increase in filling rate into the insertion apparatus 30 and the main body 100 by using a cooling mechanism 120 can be prevented.

In the present embodiment, to shorten the cooling time, TMs is calculated based upon the bending state of the superelastic alloy 71, and after the temperature of the superelastic alloy 71 has reached TAf, the temperature of the superelastic alloy 71 is decreased to the calculated TMs. Thus, the superelastic alloy 71 is in a waiting state to change from the high-rigidity state to the low-rigidity state. Then, when the superelastic alloy 71 actually changes from the high-rigidity state to the low-rigidity state, the cooling allows the superelastic alloy 71 to change from the high-rigidity state to the low-rigidity state in a short time.

The rigidity variable controller 103 calculates the target temperature TMs based upon the bending amount x of the superelastic alloy 71 detected by the bending state detection sensor 80 and the equation (1) or (2) prestored in the storage 105. Specifically, upon receiving the bending amount κ of the superelastic alloy 71 from the bending state detection sensor 80, the rigidity variable controller 103 gains access to the storage 105 and calculates the target temperature TMs based upon the bending amount κ of the superelastic alloy 71 and the equation (1) or (2). Thus, TMs can be calculated in a short time, and the temperature of the superelastic alloy 71 can be controlled to change from TAf to TMs in a short time. Since the storage 105 stores the equation (1) or (2) in advance, the load of the rigidity variable controller 103 in the calculation can be reduced.

The rigidity variable controller 103 may gain access to the storage 105 that stores a data table and calculate TMs corresponding to the bending amount κ from the data table. TMs can thus be calculated in a short time, and the temperature of the superelastic alloy 71 can be controlled to change from TAf to TMs in a short time. Since the storage 105 stores a database in advance, the load of the rigidity variable controller 103 in the calculation can be reduced.

Figure 6:
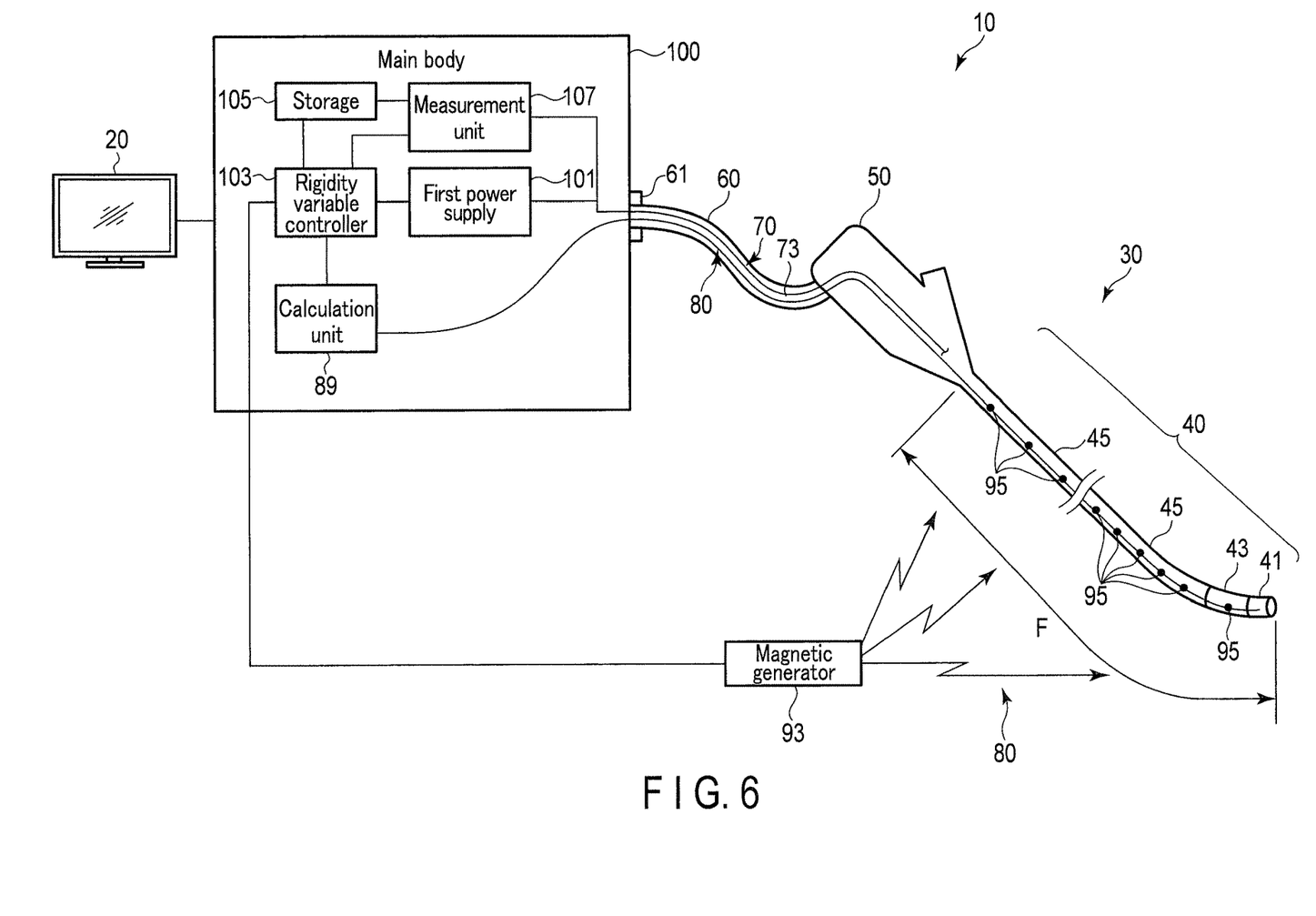
FIG. 6 is a diagram showing an example of the bending state detection sensor.

The bending state detection sensor 80 need not be limited to including a fiber sensor. As shown in FIG. 6, the bending state detection sensor 80 may include a magnetic generator 93 that generates magnetism and magnetic detection sensors 95 that detect the intensity of the magnetism generated from the magnetic generator 93. The magnetic generator 93 is placed, for example, outside an insertion target. The magnetic detection sensors 95 are placed, for example, in a portion where at least the rigidity variable portion 70 can vary the rigidity of the insertion section 40. In other words, the magnetic detection sensors 95 are arranged in a portion where the superelastic alloy 71 is placed, such as the whole portion of the flexible tube section 45. The magnetic detection sensors 95 are arranged, for example, at regular intervals in the longitudinal axis direction of the insertion section 40. The magnetic detection sensors 95 are, for example, coil magnetic sensors. Furthermore, the magnetic generator 93 generates different magnetic fields by coils. The intensity of magnetism detected by the magnetic detection sensors 95 varies with the distance between the insertion section 40 and the magnetic generator 93. Thus, the calculation unit 89 calculates positional information of each of the magnetic detection sensors 95 with respect to the magnetic generator 93 based upon the intensities of magnetisms that are detection results in which the magnetic detection sensors 95 have detected different magnetisms generated by the magnetic generator 93. Based on the positional information of each of the magnetic detection sensors 95, the calculation unit 89 calculates the bending state of the rigidity variable portion 70 (e.g. the superelastic alloy 71). Note that magnetic generators 93 may be arranged in the interior of the insertion section 40 and a single magnetic detection sensor 95 may be placed outside the insertion target.

The bending state detection sensor 80 may detect a bending shape using X rays, for example.

In the present embodiment, the display 20 may display the bending amount of the insertion section 40 and the bending amount of the superelastic alloy 71, detected by the bending state detection sensor 80. An operator of the insertion system 10 confirms the bending amounts displayed on the display 20. The operator may provide the rigidity variable portion 70 with a turn-on or turn-off instruction through the rigidity variable controller 103, using an instruction unit (not shown) to vary the rigidity of the superelastic alloy 71 in Steps 2 and 12 based upon the bending amounts displayed on the display 20. In other words, the rigidity variable controller 103 may control the temperature of the rigidity variable portion 70 based upon the bending state of the rigidity variable portion 70 that has been detected by the bending state detection sensor 80, displayed on the display 20, and confirmed by the operator.

The display 20 may also display the temperature of the rigidity variable portion 70 measured by the measurement unit 107. The operator confirms the temperature of the rigidity variable portion 70 displayed on the display 20. Then, the operator may provide the rigidity variable controller 103 with an instruction to vary the rigidity of the superelastic alloy 71 using the instruction unit (not shown) in Steps 2 and 12 such that the superelastic alloy 71 may have rigidity corresponding to the temperature of the rigidity variable portion 70 displayed on the display 20.

As described above, the rigidity of the superelastic alloy 71 may be varied through manual operation.

Second Embodiment

Figure 7A:
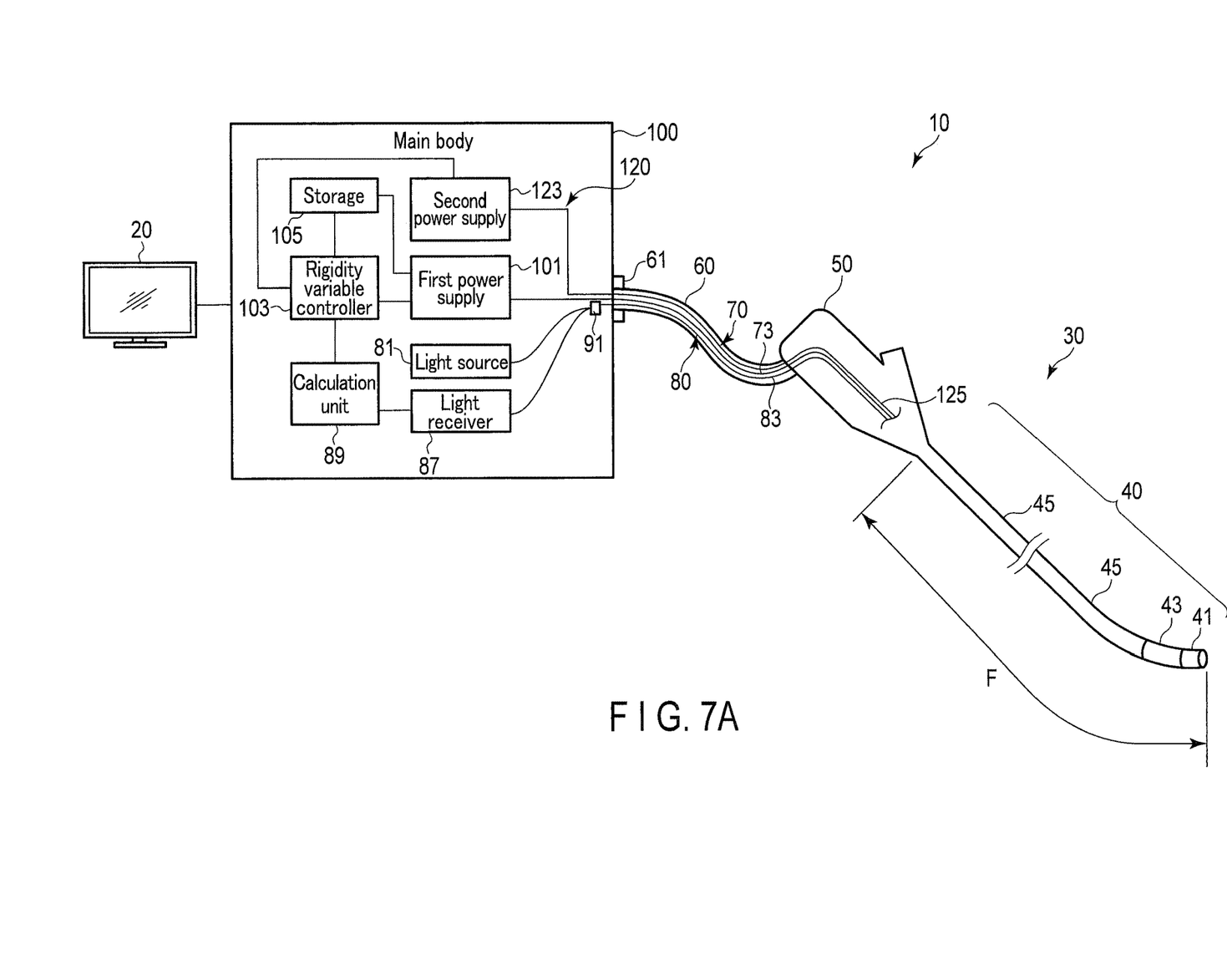
FIG. 7A is a schematic diagram of an insertion system according to a second embodiment of the present invention.

Only the points that differ from the first embodiment will be described below with reference to FIGS. 7A and 7B. In the present embodiment, cooling is performed actively. Thus, the insertion system 10 includes a cooling mechanism 120 capable of cooling the rigidity variable portion 70. The cooling mechanism 120 includes cooling elements 121 and a second power supply 123 that applies power to the cooling elements 121.

Figure 7B:
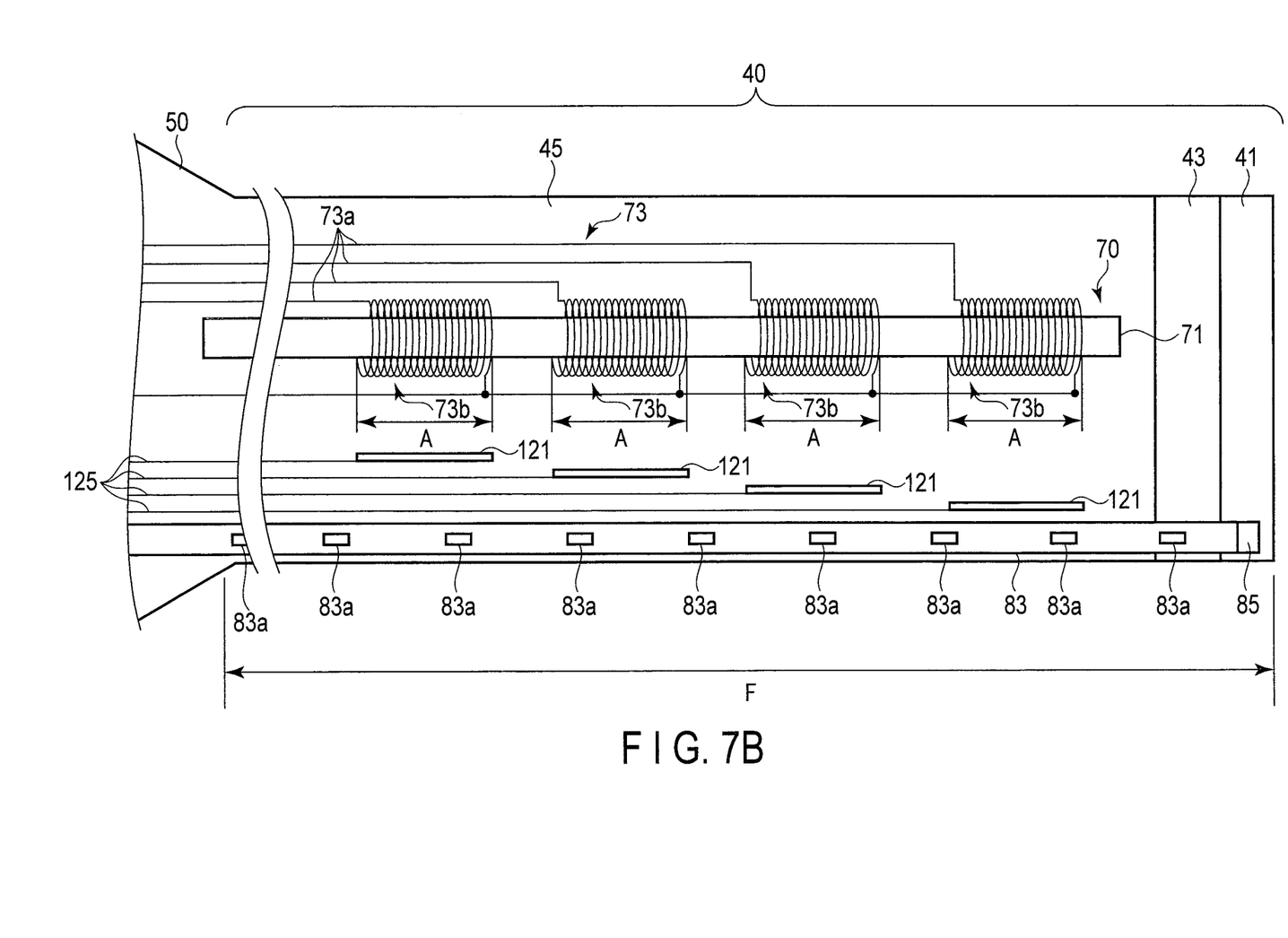
FIG. 7B is a diagram showing a configuration of each of a bending state detection sensor, a rigidity variable portion, and a cooling element in an insertion section shown in FIG. 7A.

As shown in FIG. 7B, the cooling elements 121 are arranged on the periphery of the rigidity variable portion 70. Specifically, the cooling elements 121 are arranged, for example, in the interior of the insertion section 40 and in the vicinity of the superelastic alloy 71. The cooling elements 121 directly cool the superelastic alloy 71. To show the cooling elements 121 clearly, they are arranged away from the superelastic alloy 71, but it is actually favorable that they are arranged in contact with the superelastic alloy 71. The cooling elements 121 each include, for example, a Peltier device. Favorably, the cooling elements 121 are each arranged, for example, on the periphery of a portion to be heated.

The second power supply 123 controls the cooling elements 121 through electric wires 125. The second power supply 123 is controlled by the rigidity variable controller 103. The second power supply 123 is placed in the main body 100.

Figure 5:
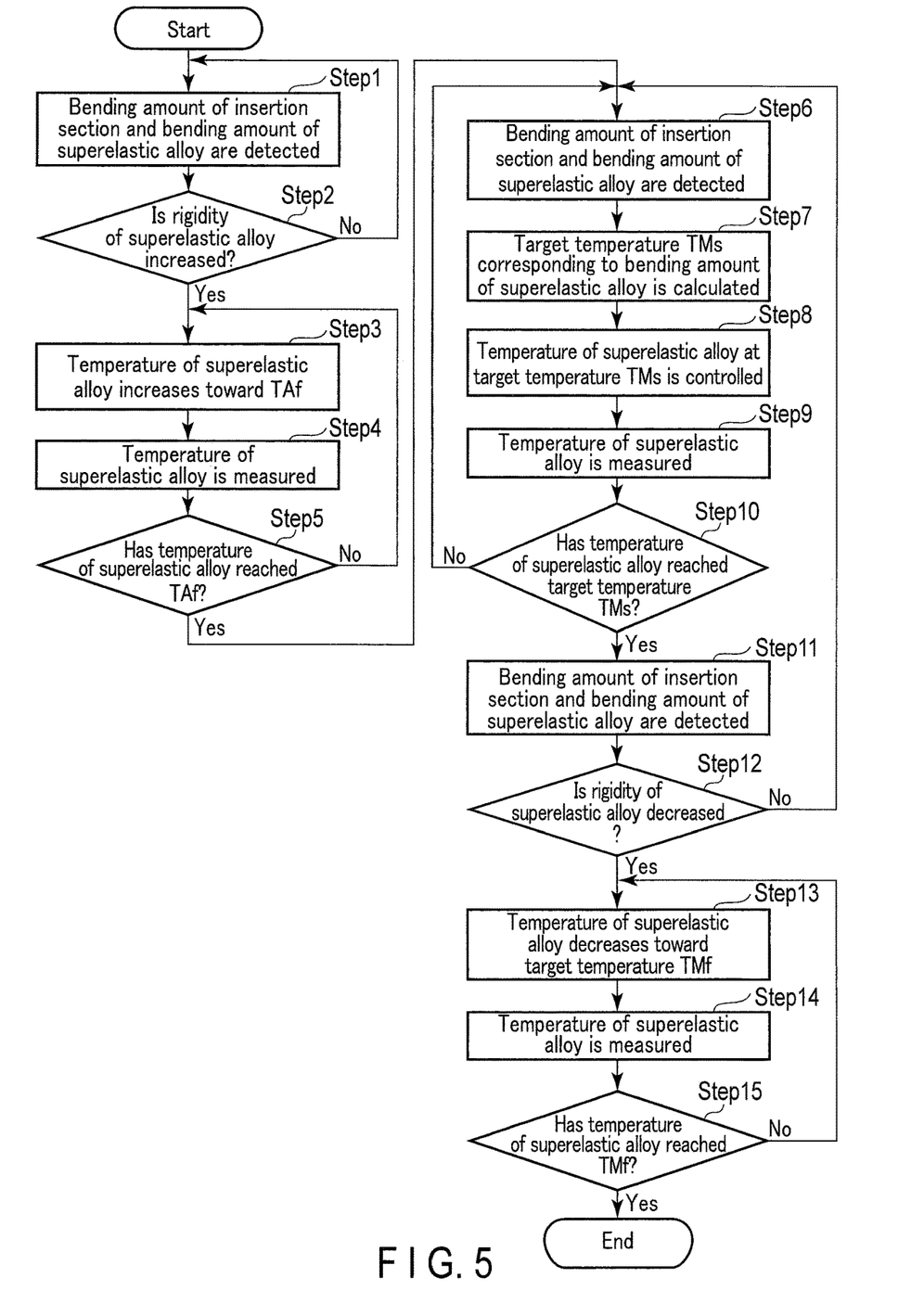
FIG. 5 is a flowchart showing part of the flow of a process in the insertion system.

In the present embodiment, in Step 3 shown in FIG. 5, the rigidity variable controller 103 controls the first power supply 101 to turn on and controls the second power supply 123 to turn off. Accordingly, the heater 73 heats the superelastic alloy 71 and the cooling elements 121 stops cooling the superelastic alloy 71. Thus, the rigidity variable controller 103 controls the temperature of the superelastic alloy 71 to change to TAf through the first power supply 101, the heating wires 73a, the second power supply 123, and the cooling element 121.

The rigidity variable controller 103 controls the cooling mechanism 120 based upon the bending state of the rigidity variable portion 70 detected by the bending state detection sensor 80. For example, in Step 8 shown in FIG. 5, the rigidity variable controller 103 controls the first power supply 101 to turn off and controls the second power supply 123 to turn on. Accordingly, the heater 73 stops heating the superelastic alloy 71 and the cooling element 121 cools the superelastic alloy 71. Then, not natural cooling but active cooling is executed to decrease the temperature of the superelastic alloy 71 toward the target temperature TMs quickly. Thus, the rigidity variable controller 103 controls the temperature of the superelastic alloy 71 to change to TMs through the first power supply 101, the heating wires 73a, the second power supply 123, and the cooling element 121.

The operation of Step 8 includes, as control after No in Step 12, control to maintain the temperature that has reached TMs and control to increase the temperature of the superelastic alloy 71 when the bending amount of the insertion section 40 varies to increase the target temperature. To maintain the temperature, the rigidity variable controller 103 controls each of the first and second power supplies 101 and 123 to turn on or turn off. To increase the temperature, the rigidity variable controller 103 controls the first power supply 101 to turn on and controls the second power supply 123 to turn off.

In Step 13 shown in FIG. 5, the rigidity variable controller 103 controls the first power supply 101 to turn off and controls the second power supply 123 to turn on. Accordingly, the heater 73 stops heating the superelastic alloy 71 and the cooling element 121 cools the superelastic alloy 71. Then, not natural cooling but active cooling is executed to decrease the temperature of the superelastic alloy 71 toward the target temperature TMf quickly. Thus, the rigidity variable controller 103 controls the temperature of the superelastic alloy 71 to change to TMf through the first power supply 101, the heating wires 73a, the second power supply 123, and the cooling element 121. When the temperature of the superelastic alloy 71 has reached TMf, the cooling is finished.

In the present embodiment, the temperature of the superelastic alloy 71 can accurately be controlled to change to TMs and TMf by the cooling mechanism 120. Since the superelastic alloy 71 can be cooled by the cooling mechanism 120 in a short time, the temperature of the superelastic alloy 71 can be decreased from TAf to TMs in a short time. Therefore, after the temperature of the superelastic alloy 71 has reached TAf, the state of the superelastic alloy 71 can be switched to a waiting state in a short time. Since TMs can be maintained reliably in the waiting state, the superelastic alloy 71 and the flexible tube section 45 can be maintained reliably in the high-rigidity state even in the waiting state. Since, furthermore, the superelastic alloy 71 can be cooled by the cooling mechanism 120 in a short time, the temperature of the superelastic alloy 71 can be decreased from TMs to TMf in a short time. Therefore, the rigidity state of the superelastic alloy 71 and the flexible tube section 45 can be switched from a high-rigidity state to a low-rigidity state in a short time.

Though not shown, the cooling mechanism 120 may cool the superelastic alloy 71 by water or air if it can cool the superelastic alloy 71 actively. The cooling mechanism 120 includes a cylindrical flow path portion through which a cooling fluid flows and a circulation portion in which the cooling fluid flowing through the flow path portion is circulated. The flow path portion is flexible. The flow path portion is placed on the periphery of the rigidity variable portion 70. The flow path portion is placed, for example, in the interior of the insertion apparatus 30 including the insertion section 40. A heat radiation member (not shown) such as a heat sink is provided on the outer surface of the flow path portion. The heat radiation member is located away from the rigidity variable portion 70, such as in the interior of the control section 50. The circulation portion is placed outside the insertion apparatus 30 and includes, for example, a pump. The cooling fluid absorbs heat from the rigidity variable portion 70, and sends and transmits the heat to the heat radiation member. The heat is discharged outside the insertion apparatus through the heat radiation member.

The present invention is not limited to the above embodiments themselves. When the invention is reduced to practice, its structural elements can be modified and embodied without departing from the spirit of the invention. Furthermore, a variety of inventions can be made by appropriate combinations of the structural elements of the above embodiments.

What is claimed is:

1. An insertion system comprising:
an insertion section to be inserted into an insertion target;
a rigidity variable portion provided in the insertion section and including a superelastic alloy member whose rigidity finishes changing from a low-rigidity state to a high-rigidity state with a change from a temperature that is lower than a first temperature to a temperature that is equal to or higher than the first temperature and starts changing from the high-rigidity state to the low-rigidity state with a change to a temperature that is equal to or lower than a second temperature that is lower than the first temperature, the second temperature varying with a degree of bending of the superelastic alloy member, and a heating member capable of switching between presence and absence of heating of the superelastic alloy member;
a bending state detection sensor that detects a bending state including information of the degree of bending of the rigidity variable portion; and
a one or more processors configured to:
set a target temperature to maintain the superelastic alloy member in the high-rigidity state at a temperature that is lower than the first temperature and equal to or higher than the second temperature, based upon the information of the degree of bending after the rigidity of the superelastic alloy member changes to the high-rigidity state, and
control switching between presence and absence of heating of the superelastic alloy member by the heating member to thereby control the superelastic alloy member to change to the target temperature.

2. The insertion system according to claim 1, wherein:
a relationship between the temperature of the rigidity variable portion and the rigidity of the rigidity variable portion has a hysteresis;
when the first temperature is referred to as TAf and the second temperature is referred to as TMs, the rigidity variable controller calculates the TMs based upon the bending state of the rigidity variable portion, sets the TMs at the target temperature, and controls the temperature of the rigidity variable portion to change to the calculated TMs after the temperature of the rigidity variable portion has reached the TAf.

3. The insertion system according to claim 2, wherein when a bending amount in the bending state of the rigidity variable portion detected by the bending state detection sensor is referred to as κ, the one or more processors calculate the TMs using an equation below based upon a relationship between the premeasured bending amount κ and TMs corresponding to the bending amount:

$$TMs = A \times \log_B \kappa + C \qquad (2)$$

where, A, B, and C are constants that depend upon the premeasured bending amount and the TMs.

4. The insertion system according to claim 2, further comprising a storage that, when a bending amount in the bending state of the rigidity variable portion detected by the bending state detection sensor is referred to as κ, stores a data table showing a relationship between the κ and the TMs corresponding to the κ,
wherein the one or more processors calculate the TMs corresponding to the κ from the data table.

5. The insertion system according to claim 1, further comprising a cooling mechanism capable of cooling the rigidity variable portion,
wherein the one or more processors control the cooling mechanism based upon the bending state of the rigidity variable portion.

6. The insertion system according to claim 1, wherein the bending state detection sensor includes a fiber sensor.

7. The insertion system according to claim 1, wherein the bending state detection sensor includes:
a magnetic generator that generates magnetism;
a magnetic detection sensor that detects the magnetism generated from the magnetic generator; and
the one or more processors calculate the bending state of the rigidity variable portion based upon a detection result of the magnetic detection sensor.

8. The insertion system according to claim 1, comprising an endoscope including the insertion section.

* * * * *